(12) United States Patent
Wang et al.

(10) Patent No.: US 12,334,106 B1
(45) Date of Patent: Jun. 17, 2025

(54) APPROACHES TO VERIFYING THE IDENTITY OF SPEAKERS THROUGH OBJECTIVE, ALGORITHMIC CHARACTERIZATIONS OF VOICE FEATURES AND SYSTEMS FOR IMPLEMENTING THE SAME

(71) Applicant: Verily Life Sciences LLC, Mountain View, CA (US)

(72) Inventors: Rui Wang, Palo Alto, CA (US); Andrew Campbell, Norwich, VT (US); Danielle Schlosser, South San Francisco, CA (US); Dan Duong, Los Altos Hills, CA (US); Bret Peterson, Lafayette, CA (US); Collin Walter, South San Francisco, CA (US); Menachem Fromer, Newton, MA (US); Arthur Brant, Mountain View, CA (US); Honor Hsin, Palo Alto, CA (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

(21) Appl. No.: 18/670,436

(22) Filed: May 21, 2024

Related U.S. Application Data

(62) Division of application No. 16/184,645, filed on Nov. 8, 2018, now abandoned.

(Continued)

(51) Int. Cl.
*G10L 25/66* (2013.01)
*A61B 5/00* (2006.01)
(Continued)

(52) U.S. Cl.
CPC ............ *G10L 25/66* (2013.01); *A61B 5/0004* (2013.01); *A61B 5/117* (2013.01); *A61B 5/4803* (2013.01);
(Continued)

(58) Field of Classification Search
CPC ....................................................... G10L 25/66
See application file for complete search history.

(56) References Cited

U.S. PATENT DOCUMENTS

| 8,924,236 B2 | 12/2014 | Marchosky |
| 9,058,816 B2 | 6/2015 | Lech et al. |

(Continued)

*Primary Examiner* — Bryan S Blankenagel
(74) *Attorney, Agent, or Firm* — Perkins Coie LLP

(57) ABSTRACT

Introduced here are approaches to dynamically verifying the identity of an individual and assessing the health of the individual through objective, algorithmic characterizations of voice features derived from audio recordings created by the individual. These voice features may be paralinguistic features, non-linguistic features, or linguistic features. By characterizing these voice features, insights can be gleaned into how events represented in the audio recordings should be emotionally characterized. For example, for each audio recording created by the individual, a health management platform may calculate a valence measure that is based on the voice features established for that audio recording. These valence measures can be documented, for example, in a profile maintained for the individual, such that changes in health can be detected in a more reliable, quantitative manner.

9 Claims, 8 Drawing Sheets

Related U.S. Application Data

(60) Provisional application No. 62/583,882, filed on Nov. 9, 2017.

(51) Int. Cl.
    *A61B 5/117*       (2016.01)
    *G10L 17/06*       (2013.01)
    *G10L 25/03*       (2013.01)
    *G16H 50/30*      (2018.01)

(52) U.S. Cl.
    CPC ............ *A61B 5/7203* (2013.01); *G10L 17/06* (2013.01); *G10L 25/03* (2013.01); *G16H 50/30* (2018.01)

(56) References Cited

U.S. PATENT DOCUMENTS

| | | |
|---|---|---|
| 10,405,786 B2 | 9/2019 | Sahin |
| 2004/0117215 A1 | 6/2004 | Marchosky |
| 2010/0092929 A1 | 4/2010 | Hallowell et al. |
| 2012/0277594 A1 | 11/2012 | Pryor |
| 2013/0159021 A1 | 6/2013 | Felsher |
| 2013/0241719 A1 | 9/2013 | Kunchakarra et al. |
| 2013/0297536 A1 | 11/2013 | Almosni et al. |
| 2015/0099987 A1 | 4/2015 | Bhatkar et al. |
| 2016/0022193 A1 | 1/2016 | Rau et al. |
| 2017/0095192 A1 | 4/2017 | Sadowsky et al. |
| 2019/0246235 A1* | 8/2019 | Bruser .................... G06F 3/017 |
| 2020/0075040 A1* | 3/2020 | Provost .................. G06N 3/044 |
| 2021/0256789 A1* | 8/2021 | Pasirstein ................ G07C 9/28 |
| 2021/0383929 A1* | 12/2021 | Vorenkamp ............ G16H 10/60 |
| 2022/0257175 A1* | 8/2022 | Vatanparvar ......... A61B 5/0816 |

\* cited by examiner

400

401 Acquire a media file corresponding to a journal entry

402 Process the media file

403 Analyze the media file

404 Calculate a valence measure for an event reflected in the media file

405 Assess a health state of the individual

406 Store the valence measure or the health state assessment in a memory

407 Perform an action based on the valence measure or the health state assessment

501
Acquire a media file generated by an electronic device associated with an individual 502
Receive input that specifies a privacy setting 503
Parse the media file to identify segment(s) including data pertaining solely to the individual

601
Acquire a media file corresponding to a journal entry

602
Examine audio media included in the media file

603
Identify a linguistic feature or a non-linguistic feature indicative of health state

604
Examine text media and/or video media corresponding to the audio media

605
Identify a paralinguistic feature indicative of health state

701 Acquire valence measure(s) associated with a media file

702 Examine the valence measure(s)

703 Identify variation(s) indicative of a health state

704 Assess a health state

FIGURE 7

APPROACHES TO VERIFYING THE IDENTITY OF SPEAKERS THROUGH OBJECTIVE, ALGORITHMIC CHARACTERIZATIONS OF VOICE FEATURES AND SYSTEMS FOR IMPLEMENTING THE SAME

CROSS-REFERENCE TO RELATED APPLICATION

This application is a divisional of U.S. application Ser. No. 16/184,645, filed on Nov. 8, 2018, which claims the benefit of U.S. Provisional Application No. 62/583,882, filed on Nov. 9, 2017, each of which is incorporated by reference herein in its entirety.

TECHNICAL FIELD

Various embodiments concern computer programs and associated computer-implemented techniques for assessing health state based on the content of media files created by an individual.

BACKGROUND

Contemporary research has begun exploring how media content affects emotional state. Such research has considered emotion as a predictor of media selection, an outcome of media exposure, a mediator of other psychological/behavioral outcomes resulting from media exposure, etc.

For example, several studies have examined the emotional consequences of using social media (e.g., Facebook® or Twitter®). These studies have shown that the use of social media can cause both positive feelings and negative feelings, which can facilitate or hinder the development of social capital and social connectedness. However, these studies often overlook the impact of emotional state on media content that is consumed or created by an individual.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 4 depicts a flow diagram of a process for estimating the health state of an individual based on valence measures associated with journal entries created by the individual.

FIG. 5 depicts a flow diagram of a process for identifying segment(s) of a media file that include data from a single source (e.g., a specified individual).

FIG. 6 depicts a flow diagram of a process for analyzing media content.

FIG. 7 depicts a flow diagram of a process for assessing the health state of an individual.

Figure 1:
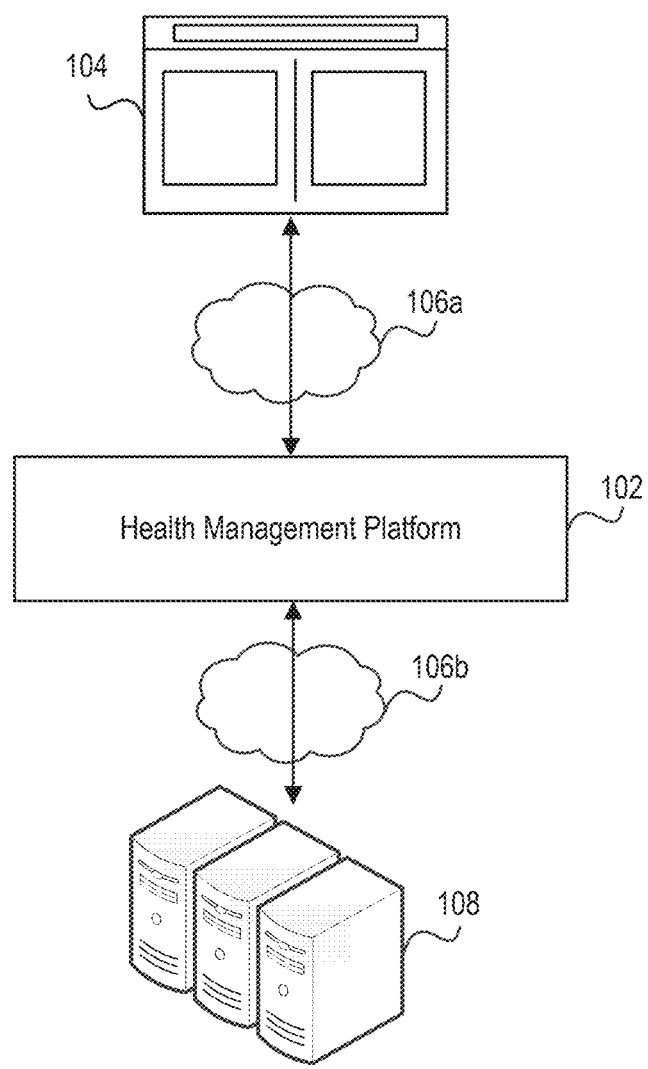
FIG. 1 illustrates a network environment that includes a health management platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Clinical interactions with patients are infrequent, so it can be difficult for a clinician to follow transitions in the health state of a patient at an optimal temporal resolution. This is particularly true for at-risk patients and patients that have recently been prescribed new medications, treatments, etc.

Entities have begun developing healthcare-focused computer programs that can automatically identify, monitor, and promote different aspects of physical, mental, and emotional well-being. Some computer programs continually track user behaviors along multiple dimensions without requiring user input. For example, a computer program may monitor user interactions with a social media platform (e.g., Facebook® or Twitter®). Classification algorithms can then be applied by the computer program. The classification algorithms enable the computer program to automatically infer different health characteristics based on the user behaviors. Health characteristics can include, for example, estimated sleep duration, physical activities, and social interactions.

However, these computer programs cannot capture much of the contextual resolution necessary to understand the health implications of various physical and social activities. For example, conventional technologies are not able to solicit freeform reporting of these activities from patients. Said another way, conventional technologies are unable to consistently solicit feedback in a non-invasive manner. Such feedback can be critical in providing diagnoses, monitoring disease or risk progression, suggesting treatment options, etc.

Introduced here, therefore, is a health management platform able to assess the health state of an individual based on the content of journal entries created by the individual. The term "health state" can refer to physical health, mental health, emotional health, or any combination thereof. For example, some embodiments of the health management platform are designed to identify/monitor features known to be indicative of depression.

More specifically, the health management platform can parse media files corresponding to journal entries to discover the personalized context of events related to an individual. An event may be a physical or social activity performed by the individual, an occasion involving the individual, etc. Because the events are reflected in the journal entries, the health management platform can determine the health state in a non-invasive manner (e.g., without directly inquiring about an event). This may be particularly useful in scenarios where individuals are less willing to expressly divulge details that are critical in determining the health state (e.g., when the health management platform is designed to monitor mental or emotional health).

A health management platform may facilitate the creation of media files by prompting the individual to periodically create journal entries. For example, the health management platform may be associated with a journal-keeping computer program that resides on an electronic device associated with the individual. Media files produced by the journal-keeping computer program can include text media, audio media, video media, or any combination thereof. For example, in some instances the individual may create text-based journal entries, while in other instances the individual may create audio-based journal entries or video-based journal entries.

After acquiring a media file corresponding to a journal entry, the health management platform can analyze the media file to determine the valence of event(s) reflected in the media file. The health management platform can assess the health state of an individual based on these valence measure(s). Such analysis can examine a paralinguistic feature, a non-linguistic feature, a linguistic feature, or any combination thereof.

Paralinguistic features refer to those aspects of communication that do not involve speech. Paralinguistic features often add emphasis or shades of meaning to what an individual says. Example of paralinguistic features include body language, gestures, facial expressions, etc. Non-linguistic features refer to those aspects of spoken communication that do not involve words. Much like paralinguistic features, non-linguistic features can add emphasis or shades of meaning to what an individual says. Examples of non-linguistic features include tone, pitch, volume/loudness, speaking rate, shimmer, jitter, etc. Linguistic features, meanwhile, refer to those aspects of spoken communication that do involve words. Examples of linguistic features include the word count of different n-grams, whether jargon/slang is used, etc.

Because it is common for electronic devices to be left accessible or shared amongst multiple individuals, some embodiments of the health management platform periodically verify identity to ensure that any data examined by the health management platform pertains to a single individual. In such embodiments, the health management platform can parse a media file to identify those segment(s) that include data from a single source (e.g., a specified individual). The segment(s) can be identified based on a paralinguistic feature, a non-linguistic feature, a linguistic feature, or a combination of such features known to be indicative of the individual. For example, some embodiments of the health management platform verify identity via facial recognition, while other embodiments of the health management platform verify identity via tone/pitch recognition.

Similarly, some embodiments of the health management platform enable the individual to toggle the privacy settings associated with the journal entries. These privacy settings may enable the individual to specify which portion(s) of a journal should be shared, what type(s) of analysis should be performed, etc. For example, the individual may specify that only audio-based journal entries should be examined by the health management platform. As another example, the individual may specify that only features that correlate with depression should be analyzed by the health management platform.

Embodiments may be described with reference to particular computer programs, system configurations, networks, etc. However, those skilled in the art will recognize that these features are equally applicable to other computer program types, system configurations, network types, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program an electronic device to perform a process for parsing media files corresponding to journal entries, calculating valence measures for events reflected in the media files, determining a health state based on the valence measures, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For instance, steps could be added to, or removed from, the processes described here. Similarly, steps could be replaced or reordered. Thus, descriptions of any processes are intended to be open-ended.

Technology Overview

FIG. 1 illustrates a network environment 100 that includes a health management platform 102. An individual can interface with the health management platform 102 via an interface 104. In some embodiments, the health management platform 102 is associated with a journal-keeping computer program that resides on an electronic device associated with the individual. Thus, the health management platform 102 may be responsible for periodically prompting the individual to create journal entries.

The health management platform 102 can then examine the journal entries to estimate the valence of events reflected in the journal entries. More specifically, the health management platform 102 can calculate a valence measure for each event reflected in a journal entry. Valence concerns the intrinsic attractiveness ("goodness") or averseness ("badness") of an event. Consequently, a valence measure produced by the health management platform 102 can characterize the specific emotional state(s) provoked by a corresponding event. For example, anger and fear have negative valence measures, while joy and excitement have positive valence measures.

The health management platform 102 can examine freeform journal entries rather than, or in addition to, feedback expressly solicited from the individual (e.g., via manually-populated forms). Such action allows the health management platform 102 to determine the health state of the individual in a non-invasive manner. Moreover, because the individual is more likely to provide freeform journal entries, such action allows the health management platform 102 to readily maintain a holistic view of the health state over time. The health management platform 102 may also be responsible for creating interfaces through which the individual can create journal entries, review prior journal entries, view estimations of health state, manage preferences, etc.

The health management platform 102 may facilitate the creation of journal entries. For example, the health management platform 102 may be associated with a journal-keeping computer program that resides on an electronic device associated with the individual. In such embodiments, the health management platform 102 may cause the journal-keeping computer program to periodically generate notifications that prompt the individual to create a journal entry. Additionally or alternatively, the health management platform 102 may cause the journal-keeping computer program to generate a notification that prompts the individual to create a journal entry in response to determining that a specified event has occurred. For example, notifications may be generated in response to determining that the individual has completed an activity (e.g., accessed a social media platform, completed a physical activity, or consumed media content such as a movie) or visited a location.

Each journal entry can be associated with a corresponding media file that includes text media, audio media, and/or video media. Each journal entry may correspond to a distinct media file generated by an electronic device associated with the individual. For example, in some instances the individual may record text-based journal entries using a mobile phone, while in other instances the individual may create video-based journal entries using a tablet computer.

After acquiring a media file corresponding to a journal entry, the health management platform 102 can analyze the media file to determine the valence of event(s) reflected in the media file. Such analysis can examine a paralinguistic feature, a non-linguistic feature, a linguistic feature, or any combination thereof. The health management platform 102 can assess the health state of an individual based on the valence measure(s) associated with a journal entry, as well as identify symptoms indicative of potential risks and diseases.

As noted above, the term "health state" can refer to physical health, mental health, emotional health, or any combination thereof. For example, some embodiments of the health management platform 102 are designed to monitor features known to be indicative of depression. As another example, some embodiments of the health management platform 102 are designed to identify changes in mood based on variations in certain features (e.g., speech features or voice features).

In some embodiments, the interface 104 enables the individual who recorded the journal entry to view or initiate playback of previously-recorded journal entries, view estimations of health state, manage preferences, etc. In other embodiments, the interface 104 enables the individual to review data pertaining to some other person. In such embodiments, the individual may be referred to as a "health coach" who is responsible for monitoring the health state of another individual. Generally, a health coach is a medical professional (e.g., a physician, nurse, or psychiatrist) able to provide relevant medical advice. However, a health coach could also be a friend or a family member of the person responsible for generating journal entries.

As noted above, the health management platform 102 may reside in a network environment 100. Thus, the health management platform 102 may be connected to one or more networks 106a-b. The network(s) 106a-b can include personal area networks (PANs), local area networks (LANs), wide area networks (WANs), metropolitan area networks (MANs), cellular networks, the Internet, etc. The health management platform 102 may also communicate with electronic devices over a short-range communication protocol, such as Bluetooth® or Near Field Communication (NFC).

The interface 104 is preferably accessible via some combination of a web browser, desktop application, mobile application, or over-the-top (OTT) application. Accordingly, the interface 104 may be viewed on a personal computer, tablet computer, personal digital assistant (PDA), mobile phone, game console, music player, wearable electronic device (e.g., a watch or a fitness band), network-connected ("smart") device (e.g., a television or a home assistant device), virtual/augmented reality system (e.g., a head-mounted display), or some other electronic device.

Some embodiments of the health management platform 102 are hosted locally. That is, the health management platform 102 may reside on the electronic device used to access the interface 104. For example, the health management platform 102 may be embodied as a mobile application executing on a mobile phone. Other embodiments of the health management platform 102 are executed by a cloud computing service operated by Amazon Web Services® (AWS), Google Cloud Platform™, Microsoft Azure®, or a similar technology. In such embodiments, the health management platform 102 may reside on a host computer server that is communicatively coupled to one or more content computer servers 108. The content computer server(s) 108 can include previously-recorded journal entries, user information (e.g., profiles, credentials, and health-related information), and other assets. Additionally or alternatively, such information could be stored on the host computer server.

Certain embodiments are described in the context of network-accessible interfaces. However, those skilled in the art will recognize that the interfaces need not necessarily be accessible via a network. For example, an electronic device may be configured to execute a self-contained computer program that does not require network access. Instead, the self-contained computer program may cause necessary assets (e.g., journal entries, processing operations, rule sets linking valence measures to health risks) to be downloaded at a single point in time or on a periodic basis (e.g., weekly, daily, or hourly).

Figure 2:
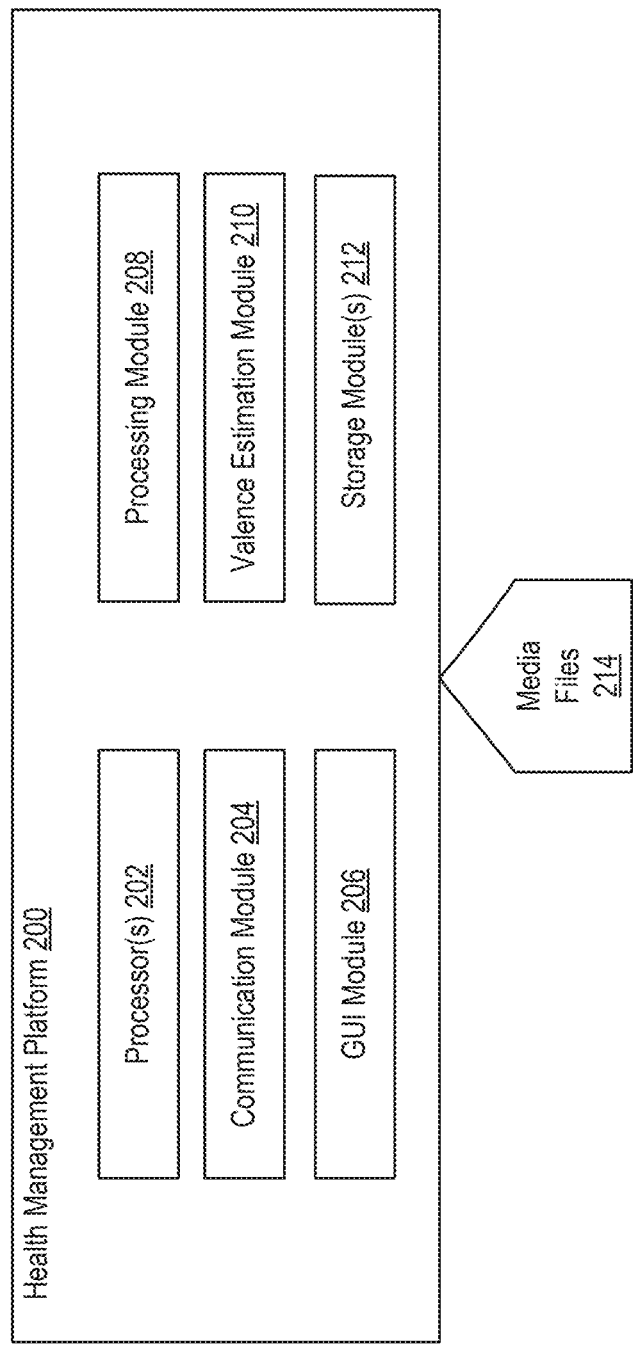
FIG. 2 depicts the high-level architecture of a health management platform able to estimate the health state of a person based on the content of journal entries produced by the person.

FIG. 2 depicts the high-level architecture of a health management platform 200 able to estimate the health state of a person based on the content of journal entries produced by the person. As shown in FIG. 1, an individual can interact with the health management platform 200 via an interface. The individual may be the person who records journal entries or another person with an interest in the health state of the person who records journal entries.

The health management platform 200 can include one or more processors 202, a communication module 204, a graphical user interface (GUI) module 206, a processing module 208, a valence estimation module 210, and one or more storage modules 212. In some embodiments a single storage module includes multiple computer programs for performing different operations (e.g., speech recognition, noise reduction, filtering, feature analysis), while in other embodiments each computer program is hosted within a separate storage module. Embodiments of the health management platform 200 may include some or all of these components, as well as other components not shown here.

The processor(s) 202 can execute modules (e.g., processing module 208 and valence estimation module 210) from instructions stored in the storage module(s) 212, which can be any device or mechanism capable of storing information. The communication module 204 can manage communications between various components of the health management platform 200. The communication module 204 can also manage communications between the electronic device on which the health management platform 200 resides and another electronic device.

For example, the health management platform 200 may reside on a mobile phone in the form of a mobile application. In such embodiments, the communication module 204 can facilitate communication with a network-accessible computer server responsible for supporting the mobile application. The communication module 204 may facilitate communication with various data sources through the use of application programming interfaces (APIs), bulk data interfaces, etc.

As another example, the health management platform 200 may reside on a server system that includes one or more network-accessible computer servers. In such embodiments, the communication module 204 can communicate with a computer program executing on the electronic device associated with the individual. Those skilled in the art will recognize that the components of the health management platform 200 can be distributed between the server system and the electronic device associated with the individual in various manners. For example, some data (e.g., media files corresponding to journal entries) may reside on the electronic device of the individual, while other data (e.g., processing operations, speech recognition algorithms, valence estimation algorithms, rule sets linking valence measures to health risks) may reside on the server system.

The GUI module 206 can generate the interfaces through which an individual can interact with the health management platform 200. For example, an interface may include a graphical representation of the current health state or the health state over a specified period of time. As another example, an interface may include media content based on the current health state. For instance, uplifting media content may be shown in response to determining that the individual has experienced event(s) having negative valence (e.g., causing a downward shift in mood or emotion), while supportive media content may be shown in response to determining that the individual has experienced event(s) having positive valence (e.g., causing an upward shift in mood or emotion). These interfaces may also present suggestions for improving the health state. For example, if the health management platform 200 determines that the individual has experienced event(s) having negative valence, then the health management platform 200 may recommend that the individual perform activities known to have positive valence. That is, the health management platform 200 may recommend the individual perform activities known to improve the health state.

The processing module 208 can apply one or more operations to media files 214 acquired by the health management platform 200. Generally, each media file corresponds to a different journal entry produced by the individual. Media files 214 could include text media, audio media, video media, or any combination thereof. For example, some media files may only include text media, some media files may include only audio media, and some media files may include audio and video media. The health management platform 200 can simultaneously or sequentially process media files having different types of content. Accordingly, some individuals may create a single type of journal entry (e.g., text-based journal entries), while other individuals may create multiple types of journal entries (e.g., text-based journal entries and audio-based journal entries).

The health management platform 200 acquires the media files 214 from one or more different sources. For example, an individual may create some journal entries on a mobile phone and other journal entries on tablet computer. The health management platform 200 can be configured to retrieve media files created by each of these electronic devices. Generally, the health management platform 200 will monitor all electronic devices the individual has identified as being possible sources of media files. Thus, journal entries may be recorded by any number of electronic devices.

An electronic device may be configured to periodically transmit media files 214 to the health management platform 200. In some embodiments, the electronic device uploads media files to the health management platform 200 so long as the electronic device remains communicatively coupled to the health management platform 200. Thus, the electronic device may automatically upload a media file in response to determining that the individual has finished creating the corresponding journal entry. In other embodiments, the electronic device uploads a data set of media file(s) to the health management platform 200 on a periodic basis (e.g., hourly, daily, or weekly). In such embodiments, the data set may include multiple media files corresponding to different journal entries created over a specified time period. For example, a single data set may include seven different media files corresponding to daily journal entries created over the course of a week.

The processing module 208 can process the media files 214. For example, if a media file includes audio media, then the processing module 208 may apply noise reduction algorithms or filtering algorithms to improve the signal-to-noise (SNR) ratio. Moreover, the processing module 208 may apply speech recognition algorithms to create a transcript of words spoken within the media file. The processing module 208 can also analyze the media files 214 to identify one or more features indicative of the health state. Such analysis can examine a paralinguistic feature, a non-linguistic feature, a linguistic feature, or any combination thereof.

Paralinguistic features refer to those aspects of communication that do not involve speech. Paralinguistic features often add emphasis or shades of meaning to what an individual says. Example of paralinguistic features include body language, gestures, facial expressions, etc. Non-linguistic features refer to those aspects of spoken communication that do not involve words. Much like paralinguistic features, non-linguistic features can add emphasis or shades of meaning to what an individual says. Examples of non-linguistic features include tone, pitch, volume/loudness, speaking rate, shimmer, jitter, etc. Linguistic features, meanwhile, refer to those aspects of spoken communication that do involve words. Examples of linguistic features include the word count of different n-grams, whether jargon/slang is used, etc.

Non-linguistic and linguistic features can generally be grouped into two categories: speech features and voice features.

Speech features are typically discovered by applying speech recognition algorithm(s) on audio or video media. For example, the processing module 208 may initially detect speech in a media file to create a transcript of audio media included in the media file, and then identify speech feature(s) based on the transcript. Examples of speech features include:

Sentiment Analysis—A natural language API can be adapted to estimate sentiment based on text media. Estimated sentiments can include two values: a sentiment score between
−1.0 (negative sentiment) and +1.0 (positive sentiment), and a non-negative magnitude number that represents the absolute magnitude of sentiment regardless of whether the sentiment score is positive or negative.

Word Count—Word count specifies the total number of words spoken within a media file.

Speaking Rate—Speaking rate specifies how fast words are spoken. Speaking rate is generally measured by diving the total number of words spoken within a media file by the duration of the media file.

Word Count of N-grams—Prior studies have found connections between the language used in social media (e.g., on Facebook® or Twitter®) and health state. Thus, the processing module 208 may detect the total number of words in certain n-gram categories that correlate with health state. Moreover, the processing module 208 may detect strings of multiple words corresponding to certain n-gram categories that are stronger indicators of health state (e.g., "severe" and "addiction" may be weaker in isolation relative to "severe addiction"). Examples of n-gram categories and representative n-grams include:

Symptoms—Anxiety, withdrawal, severe, delusions, ADHD, weight, insomnia, drowsiness, suicidal, appetite, dizziness, nausea, episodes, attacks, sleep, seizures, addictive, weaned, swings, dysfunction, blurred, irritability, headache, fatigue, imbalance, nervousness, psychosis, drowsy;

Disclosure—Fun, play, helped, god, answer, wants, leave, beautiful, suffer, sorry, tolerance, agree, hate, helpful, haha, enjoy, social, talk, save, win, care, love, like, hold, cope, amazing, discuss;

Treatment—Medication, side effects, doctor, doses, effective, prescribed, therapy, inhibitor, stimulant, antidepressant, patients, neurotransmitters, prescriptions, psychotherapy, diagnosis, clinical, pills, chemical, counteract, toxicity, hospitalization, sedative, 150 milligram (mg), 40 mg, drugs;

Relationships/Life—Home, woman, man, she, him, girl, boy, game, friends, sexual, someone, movie, favorite, jesus, house, music, religion, her, songs, party, bible, relationship, hell, young, style, church, lord, father, season, heaven, dating;

Depression-Indicative—Loser, depressed, depression, depressing, lonely, sad, alone, weak, useless, life, imbalance, blame, problems, unsuccessful, suicidal, torture, safe, escape, worry, intimidate, uncomfortable, therapy, medication, pressure, conversation hurts, myself, worth, break, nobody, mine, painful, hate, suck; and Standard—Work, weekend, lol, say, friends, brilliant, follow, tips, love, amazing, hello, now, bored, awesome, beautiful, romantic, perfect, excited, smile, meet, tonight, life, movie, football, favorite, sleepy, great, night, team, good, anyone, you, your, tomorrow, money.

The valence estimation module 210 can calculate a valence measure for an event reflected in a media file based on these speech features. For example, increased depression has been associated with a decrease in speaking rate in comparison to prior recordings. As another example, certain n-gram categories (e.g., symptoms, treatment, and depression-indicative) have been shown to correlate with depression while other n-gram categories (e.g., disclosure, relationships/life, standard) have been shown to correlate with non-depression. The valence estimation module 210 may examine the total number of terms within these n-gram categories, the ratio of terms within separate n-gram categories, increases/decreases in the total number of terms within a certain n-gram category over time, etc.

Voice features are typically discovered by applying processing algorithm(s) on audio or video media. For example, the processing module 208 may detect a voice feature based on a time-domain feature and/or a frequency domain feature of an audio signal. The audio signal may be associated with audio or video media. Examples of voice features include:

Recording Duration—Recording duration specifies the total duration of the audio signal, which can be measured by dividing the total number of audio samples by the sample rate.

Pitch—Pitch (also referred to as the "fundamental frequency") specifies the frequency of vocal fold vibration. Pitch correlates with changes in vocal fold tension and subglottal air pressure. Child speech typically ranges from 250-400 hertz (Hz), while adult females tend to speak around 200 Hz and adult males tend to speak around 125 Hz. The processing module 208 can, for example, set a specified frequency range (e.g., 80-525 Hz) and ignore pitches detected outside of the specified frequency range. Pitch has been found to correlate with health state. For example, increased depression has been associated with a decrease in pitch in comparison to prior audio samples produced by the same individual. Increased depression has also been associated with decreased levels of pitch variability (e.g., increases in monotone speech).

Formant Frequencies/Bandwidths—In phonetics, formant can refer to either the resonance or the spectral maximum that the resonance produces. The processing module 208 can estimate formant frequencies, bandwidths, or both. For example, the processing module 208 may compute the center frequency of the first formant (Formant $F_1$), the second formant (Formant $F_2$), or the third formant (Formant $F_3$). Formant frequencies have been found to correlate with health state. For example, increased depression and psychomotor retardation have been associated with changes in formant frequency (e.g., mean and standard deviation).

Average Pause Duration—Average pause duration specifies the mean duration of pauses included in the audio signal. Such analysis typically relies on pitch detection. For example, the processing module 208 may identify those regions of the audio signal where the fundamental frequency exists (referred to as "voiced regions") and those regions of the audio signal where the fundamental frequency does not exist (referred to as "pause regions"). Various pause-related features have been found to be predictive of depression.

Normalized Pause Count—Normalized pause count can be measured by dividing the total number of pauses by the duration of the audio signal. Increased depression has been associated with more frequent pauses.

Percent Pause Time—Percent pause time can be measured by dividing the duration of all pause regions by the duration of the audio signal. Increased depression has been associated with increased pause time.

Vocalization/Pause Rati—Vocalization/pause ratio can be measured by diving the duration of all voiced regions by the duration of all pause regions.

Loudness—Loudness specifies the perceived signal intensity along the auditory spectrum. Loudness can be measured by summing over all bands of the auditory spectrum (i.e., the Mel-frequency scale from 20-8,000 Hz). Increased depression has been associated with decreased loudness. Some embodiments employ the following loudness function:

$$E(f) = \frac{10^{31} \cdot \left((2\pi f)^2 + 56.8 \times 10^6\right)(2\pi f)^4}{\left((2\pi f)^2 + 6.3 \times 10^6\right)^2 \cdot \left((2\pi f)^2 + 0.38 \times 10^9\right)\left((2\pi f)^7 + 1.7 \times 10^{31}\right)}.$$

Shimmer—Shimmer specifies the short-term (e.g., cycle-to-cycle) variation in pitch amplitude. Shimmer has been found to be associated with psychomotor retardation and depression. For example, increased depression has been associated with increased levels of shimmer.

Jitter—Jitter specifies the short-term (e.g., cycle-to-cycle) variation in fundamental frequency. Jitter has been found to be associated with psychomotor retardation and depression. For example, increased depression has been associated with increased levels of jitter.

Harmonics-to-Noise Ratio (HNR)—HNR is a voice quality measure that measures aspiration. Increased depression has been associated with lower levels of HNR. Some embodiments employ the following HNR function:

$$HNR_{acf} = \frac{AFC_{T_0}}{ACF_0 - ACF_{T_0}}.$$

Alpha Ratio—The alpha ratio is defined as the ratio between the summed sound energy in the spectrum below and above 1,000 Hz. The alpha ratio, which is expressed in decibels (dB), is dependent on subglottal pressure and loudness but can also be influenced by formant characteristics. The alpha ratio is generally low when experiencing fear, anger, and joy. The alpha ratio is generally high when experiencing sadness and relief.

Hammarberg Index—The Hammarberg index is defined as the ratio of the strongest energy peak in the 0-2 kilohertz (kHz) region to the strongest energy peak in the 2-5 kHz region.

Spectral Slope—A spectral slope is the linear slope that describes the overall shape of a spectrum. More specifically, the spectral slope is the coefficient of the ordinary least squares (OLS) regression over the spectral bin energies. The processing module 208 may, for example, calculate the spectral slope over different frequency ranges (e.g., 0-500 Hz, 500-1,500 Hz, 1,000-1,500 Hz).

Harmonic Difference—The processing model 208 may examine the difference in energy between the first harmonic (H1) and the second harmonic (H2), the first harmonic (H1) and the third harmonic (H3), etc.

Spectral Flux—Spectral flux represents a quadratic and normalized spectral difference of two consecutive signal frames.

Zero Crossing Rate (ZCR)—ZCR describes the number of sign changes per second. A high ZCR value is indicative of an audio signal with high frequency content.

Spectral Centroid—Spectral centroid represents the center of gravity of a spectrum (X(m)). Some embodiments calculate the spectral centroid as follows:

$$S_{centroid} = \frac{\sum_{m=m_1}^{m_u} F(m)X(m)}{\sum_{m=m_1}^{m_u} X(m)}.$$

Spectral Spread—Spectral spread represents the variance in the spectral energy. Some embodiments calculate the spectral spread as follows:

$$S_{variance} = S_\sigma^2 = \sum_{m=m_1}^{m_u} (F(m) - S_{centroid})^2 px(m).$$

Spectral Energy Entropy—Lower spectral entropy is associated with many distinct spectral peaks, whereas higher spectral entropy is associated with a flat spectrum.

Spectral Roll-off Point—The spectral roll-off point represents the frequency below which 95% of the spectral energy resides.

Mel-Frequency Cepstral Coefficients (MFCC)—The mel-frequency cepstrum (MFC) is a representation of the short-term power spectrum of an audio signal. The MFCCs are the coefficients that collectively make up the MFC. The processing module 208 can examine, for example, the first four MFCCs corresponding to an audio signal.

The valence estimation module 210 can use these speech features and/or voice features to estimate the valence of event(s) reflected in the media file. Valence concerns the intrinsic attractiveness ("goodness") or aversiveness ("badness") of an event, object, or situation. The term "valence" can be used to characterize and categorize specific emotional states. For example, anger and fear have negative valence measures, while joy and excitement have positive valence measures.

More specifically, the valence estimation module 210 can calculate a valence measure for each event using at least one feature. A valence measure may be based on the valence measure associated with a single feature or the valence measures associated with multiple features. For example, some embodiments of the valence estimation module 210 calculate valence measures using a combination of speech features and voice features.

Generally, the valence estimation module 210 uses both speech feature(s) and voice feature(s) to calculate valence measures. For example, the valence estimation module 210 may determine that the individual is experiencing negative valence based on a combination of the valence measures associated with speaking rate, word count of n-grams, vocalization/pause ratio, and shimmer. However, in some embodiments the valence estimation module 210 only uses speech feature(s), while in other embodiments the valence estimation module 210 only uses voice feature(s).

The valence estimation module 210 may produce a separate valence measure for each feature of multiple features (e.g., speech features and/or voice features). For example, the valence estimation module 210 could calculate a valence measure for a speech feature and another valence measure for a voice feature. The valence estimation module 210 may compare the multiple valence measures to ensure consistency, accuracy, etc.

In some instances, the valence estimation module 210 may determine that the valence measures are indicative of dissimilar valences. For example, the valence measure for a speech feature may be indicative of positive valence, while the valence measure for a voice feature may be indicative of negative valence. As another example, the valence measure for a non-linguistic feature or linguistic feature may be indicative of positive valence, while the valence measure for a paralinguistic feature (e.g., a facial expression) may be indicative of negative valence. These dissimilarities are often of interest in examining the disconnect between context and subconscious features. Accordingly, the valence estimation module 210 may identify the corresponding media file as a salient signal worthy of further review (e.g., by a medical professional).

Moreover, the valence estimation module 210 may assess the health state of an individual based on the valence measure(s). For example, some embodiments of the valence estimation module 210 monitor the valence measure(s) associated with feature(s) known to be indicative of depression. As another example, some embodiments of the valence estimation module 210 identify valence measure(s) that exceed a specified threshold, and thus are indicative of certain moods (e.g., anger, sadness, or frustration).

Figure 3:
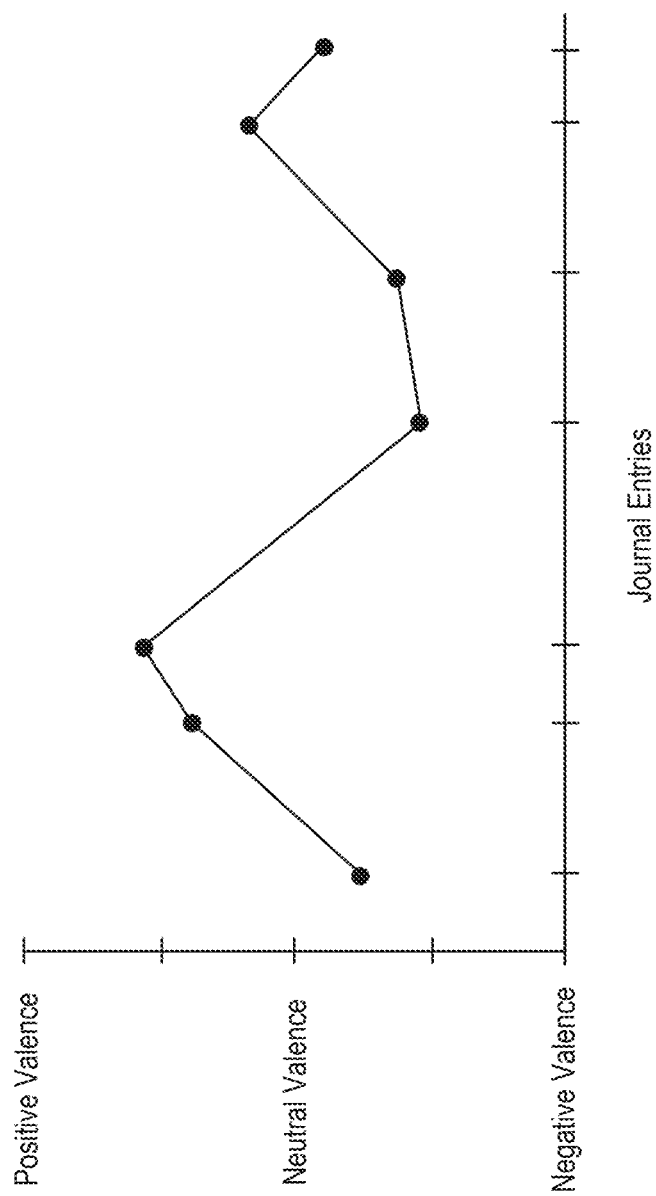
FIG. 3 illustrates how the health state of an individual can vary over a time period (e.g., day, week, or month).

FIG. 3 illustrates how the health state of an individual can vary over a time period (e.g., day, week, or month). As shown here, a health management platform (e.g., health management platform 200 of FIG. 2) can calculate a valence measure for each journal entry created by the individual. Such action enables the health management platform to establish a holistic picture of the health state in a non-invasive manner.

The health management platform can monitor several different metrics in order to discover the appropriate time to notify the individual or some other person that additional action(s) may be necessary. For example, the health management platform may monitor the valence measures to detect any valence measures that exceed a lower threshold (i.e., a specified negative valence). As another example, the health management platform may monitor valence measures to detect a specified number of consecutive negative valence measures. Consecutive negative valence measures may be flagged for further review. Similarly, the health management platform may monitor the overall valence trend (e.g., whether valence values are trending upward or downward).

Generally, correlation between feature(s) and a specified health condition (e.g., depression) is discovered by examining a cohort of individuals. For example, a health management platform may determine that a certain feature is predictive of depression onset by observing those individuals in the cohort that have been diagnosed with depression.

However, the features themselves can be highly personalized based on the characteristics of an individual. For example, even if the health management platform determines that decreased loudness is indicative of increased depression, the health management platform may not categorize an individual as being at risk of depression unless a recent journal entry exhibits decreased loudness with respect to prior journal entries created by the same individual. Thus, the health management platform may examine relative shifts in features rather than the absolute values of the features.

Similarly, individuals known to be at a high risk of a certain health condition (e.g., depression) may have different feature value thresholds or valence measure thresholds than other individuals. For example, an individual who was previously diagnosed with depression may be flagged for further examination after producing two consecutive journal entries with negative valence measures, while other individuals may be flagged for further examination after producing four consecutive journal entries with negative valence measures.

Valence measures calculated using the techniques introduced here may be particularly useful when considered in conjunction with valence indicators from other sources. For example, multiple weak valence indicators corresponding to a single event may be combined to increase confidence in a valence measure calculated for the single event. Moreover, other contextual factors may affect which features (e.g., paralinguistic features, non-linguistic features, or linguistic features) are used, the threshold(s) associated with each feature, etc. For example, if an individual is known to be more susceptible to depression after interacting with a specified person (e.g., a certain family member), then the health management platform may consider the location of an electronic device associated with the individual, the schedule of the individual, etc. These factors allow the health management platform to better understand the context of event(s) experienced by the individual.

Valence measures may also be used to control how often journal entries are examined by the health management platform. For example, if the health management platform detects a specified downward change in valence, then the health management platform may request an increased cadence of production of journal entries so that changes in health state can be quickly detected. As another example, if the health management platform detects a contextual factor indicative of an increased susceptibility to changes in health state, then the health management platform may request an increased cadence of production of journal entries so that changes in health state can be quickly detected.

FIG. 4 depicts a flow diagram of a process 400 for estimating the health state of an individual based on valence measures associated with journal entries created by the individual. Such action is intended to ensure that potentially dangerous health states are rapidly identified and brought to the attention of the appropriate person(s). Moreover, because the health state can be determined in a non-invasive manner (e.g., without directly inquiring about an event), the individual may be more willing to continually provide feedback over time. This may be particularly useful in scenarios where the individual is less willing to expressly divulge details that are critical in determining the health state (e.g., when monitoring mental or emotional health).

Initially, a health management platform (e.g., health management platform 200 of FIG. 2) acquires a media file corresponding to a journal entry recorded by an electronic device associated with the individual (step 401). The journal entry can include, for example, a self-reported audio record of events or experiences associated with the individual. Generally, the health management platform automatically acquires the media file on behalf of the individual (e.g., without requiring explicit user input). However, in some embodiments the health management platform prompts the individual to confirm that the media file should be uploaded to the health management platform for review.

As noted above, the health management platform may facilitate the creation of media files by prompting the individual to periodically create journal entries. For example, the health management platform may be associated with a journal-keeping computer program that resides on the electronic device. Media files produced by the journal-keeping computer program can include text media, audio media, video media, or any combination thereof. For example, in some instances the individual may create text-based journal entries, while in other instances the individual may create audio-based journal entries.

The health management platform can process the media file (step 402). For example, if a media file includes audio media, then the health management platform may apply noise reduction algorithms or filtering algorithms to improve the SNR ratio. As another example, if the media file does not include text media, then the health management platform may apply speech recognition algorithms to create a transcript of words spoken within the media file.

The health management platform can then analyze the media file (step 403). More specifically, the health management platform can analyze the media file to identify one or more features indicative of health state. For example, the health management platform may analyze audio media corresponding to a self-reported audio record of events or experiences associated with the individual, a transcript of words uttered within the self-reported audio record, or both. Such analysis can examine a paralinguistic feature, a non-linguistic feature, a linguistic feature, or any combination thereof.

The health management platform can calculate a valence measure for an event reflected in the media file based on the identified feature(s) (step 404). As noted above, the valence measure may be based on the valence measure associated with a single feature or the valence measured associated with multiple features. For example, the health management platform may calculate the valence measure using a combination of paralinguistic features, non-linguistic features, and/or linguistic features. In some embodiments, the valence measure is calculated based on the identified feature(s) and metadata corresponding to the media file. The metadata may specify the time of day at which the journal entry was recorded, the profile associated with the individual, the type of electronic device used to capture the journal entry, the location of the electronic device when the journal entry was captured, or any combination thereof. The location of the electronic device may be manually self-reported by the individual (e.g., by specifying home, work, etc.) or automatically identified by the electronic device upon the conclusion of capturing the journal entry.

In some embodiments, the health management platform calculates a separate valence measure for each feature of multiple features. For example, the health management platform may produce a first valence measure for a paralinguistic feature, a second valence measure for a non-linguistic feature, and a third valence measure for a linguistic feature. These valence measures can be combined to produce a composite valence measure in several different ways. In some embodiments, each valence measure is given equal weight. In other embodiments, the valence measures are given different weights. Each weight may be based on the correlation coefficient between a health condition and the corresponding feature, a frequency of occurrence of the corresponding feature, etc.

The health management platform may also assess the health state of the individual based on the valence measure (step 405). The health state may relate to physical health, mental health, emotional health, or any combination thereof. For example, a single negative valence measure may be indicative of an angry emotional state. As another example, a series of consecutive negative valence measures may be indicative of an episode of depression. Thus, in some embodiments valence measures are more useful when compared to valence measures associated with prior journal entries.

The health management platform can store the valence measure or the health state assessment in a memory (step 406). For example, the health management platform may store the valence measure in a database to create a historical record of valence measures associated with the individual. The historical record of valence measures may be useful in monitoring the health state of the individual over time.

In some embodiments, the health management platform compares the health state to one or more previous health states. This can be accomplished by comparing the corresponding valence measures or the corresponding features. For example, trying to assess features in an individual de novo can be extremely difficult. However, the health management platform may examine features over consecutive time intervals to detect trends (e.g., the health management platform can more easily detect stress within an audio recording if the health management platform can compare the audio recording to other audio recordings produced by the same individual). Thus, the health management platform may benefit from a self-normalization effect. If the health management platform determines that the health state differs from a previous health state by more than a specified amount, then the health management platform can cause display of interactive feedback on an electronic device associated with the individual. For example, an interface generated by the health management platform may display health tips, initiate a connection with a health coach or a healthcare provider, facilitate a connection with a third-party computer program (e.g., another mobile application executing on a mobile phone associated with the individual) or another electronic intervention mechanism. The interactive feedback can include advice provided by a health coach, a survey, an exercise recommendation, etc.

The health management platform may also perform an action based on the valence measure or the health state assessment (step 407). For example, the health management platform may notify some other person in response to determining that the valence measures are indicative of a certain health state, such as episodes of depression or psychomotor retardation. The other person could be, for instance, a medical professional or a family member of the individual responsible for creating the journal entries. As another example, the health management platform may cause display of a notification by a computer program executing on the electronic device. The notification may specify whether a recent event provoked positive valence or negative valence. Such notifications may also promote events that provoke positive valences and warn against events that provoke negative valences.

Additionally or alternatively, the health management platform may notify a health coach responsible for monitoring the health state of the individual. For example, the health management platform may cause display of a notification by a computer program executing on an electronic device associated with the health coach. The notification may specify the valence measure, the health state assessment, etc. As another example, the health management platform may compile and transmit a report to the electronic device associated with the health coach. The report may specify the valence measure the valence measure and/or the health state assessment corresponding to the journal entry, as well as valence measure(s) and/or health state assessment(s) corresponding to previous journal entries. Thus, the report may indicate the health state of the individual over a specified time period (e.g., a day, week, or month).

Because it is common for electronic devices to be left accessible or shared amongst multiple individuals, some embodiments of the health management platform periodically verify identity to ensure that any data examined by the health management platform pertains to a single individual. FIG. 5 depicts a flow diagram of a process 500 for identifying segment(s) of a media file that include data from a single source (e.g., a specified individual).

Initially, a health management platform acquires a media file corresponding to a journal entry recorded by an electronic device associated with the individual (step 501). Generally, the health management platform automatically acquires the media file on behalf of the individual (e.g., without requiring explicit user input). However, in some embodiments the health management platform prompts the individual to confirm that the media file should be uploaded to the health management platform for review.

In some embodiments, the health management platform receives input that specifies a privacy setting that defines the scope of the analysis to be performed by the health management platform (step 502). The input may be indicative of user input provided at the electronic device. For example, the individual may be able to toggle privacy settings accessible via a mobile application executed by a mobile phone. These privacy settings may enable the individual to specify which portion(s) of a journal should be analyzed by the health management platform, what type(s) of analysis should be performed by the health management platform, etc. For example, the individual may specify that only audio-based journal entries should be examined by the health management platform. As another example, the individual may specify that only features that correlate with depression should be analyzed by the health management platform. In some embodiments, the input is also used to control the location of where subsequent steps in the process 500 are performed. For example, if the individual did not want audio media to leave a mobile phone, then the relevant models, processes, etc., could reside on the mobile phone. In such embodiments, only summary valence measures may be uploaded to a network-accessible server system.

Additionally or alternatively, the health management platform can automatically parse the media file to identify the segment(s) that include data pertaining only to the individual (step 503). The segment(s) can be identified based on a paralinguistic feature, a non-linguistic feature, a linguistic feature, or a combination of such features known to be indicative of the individual. For example, the health management platform may verify identity by comparing a facial characteristic identified via a facial recognition process to a master set of facial characteristics known to be associated with the individual. As another example, the health management platform may verify identity by comparing a linguistic/non-linguistic characteristic (e.g., pitch and formant frequencies) to a master set of linguistic/non-linguistic characteristics known to be associated with the individual.

FIG. 6 depicts a flow diagram of a process 600 for analyzing media content. Execution of the process 600 may enable a health management platform to identify one or more features that are indicative of the health state of an individual involved in creating the media content. Some or all of the steps in the process 600 may be performed during execution of step 403 of FIG. 4.

Initially, the health management platform acquires a media file corresponding to a journal entry recorded by an electronic device associated with the individual (step 601). Step 601 of FIG. 6 may be substantially similar to step 401 of FIG. 4.

The health management platform can then examine audio media included in the media file (step 602). In some embodiments the audio media is accompanied by other media (e.g., when the media file includes digital video data having audio media and video media), while in other embodiments the media file includes only audio media (e.g., when the media file represents an audio-based journal entry).

After examining the audio media, the health management platform can identify a non-linguistic feature and/or a linguistic feature indicative of the health state of a speaker responsible for producing the audio media (step 603). Non-linguistic features refer to those aspects of spoken communication that do not involve words. Examples of non-linguistic features include tone, pitch, volume/loudness, speaking rate, shimmer, jitter, etc. Linguistic features, meanwhile, refer to those aspects of spoken communication that do involve words. Examples of linguistic features include the word count of different n-grams, whether jargon/slang is used, etc. Both non-linguistic and linguistic features can be indicative of the health state of the speaker. For example, variations in certain features (e.g., loudness, shimmer, and jitter) may be indicative of certain health conditions (e.g., depression).

In some embodiments, the health management platform also examines text media and/or video media corresponding to the audio media (step 604). In some embodiments, these forms of media are included in the media file corresponding to the journal entry. For example, a media file that includes digital video data may include both audio media and video media. In other embodiments, these forms of media are derived from the media file corresponding to the journal entry. For example, if a media file only includes audio media, then the health management platform may produce corresponding text media by creating a transcript of words spoken in the media file.

After examining the text media and/or the video media, the health management platform can identify a paralinguistic feature indicative of the health state of the speaker responsible for producing the audio media (step 605). Paralinguistic features refer to those aspects of communication that do not involve speech. Examples of paralinguistic features include body language, gestures, facial expressions, etc. Thus, the health management platform may monitor facial expressions in video media in addition to speech/voice features in audio media. Those skilled in the art will recognize that the text media could be used in steps 603 and 605. Text media may be used to identify non-linguistic, linguistic, or paralinguistic features.

FIG. 7 depicts a flow diagram of a process 700 for assessing the health state of an individual. Some or all of the steps in the process 700 may be performed during execution of step 405 of FIG. 4.

Initially, a health management platform acquires one or more valence measures that are associated with a media file created by the individual (step 701). Generally, each valence measure will correspond to an event reflected in the media file. However, multiple valence measures may correspond to a single event. More specifically, the health management platform may produce multiple valence measures based on different features. For example, the health management platform may produce a first valence measure based on a first non-linguistic feature and a second valence measure based on a second non-linguistic feature. As another example, the health management platform may produce a first valence measure based on a non-linguistic feature and a second valence measure based on a paralinguistic feature.

The health management platform can then examine the valence measure(s) (step 702). Such examination can take several different forms. In some embodiments, each valence measure is compared to a specified threshold known to be indicative of a specified health state. For example, a negative valence measure of a certain value may be indicative of an angry emotional state. In other embodiments, the valence measure(s) are compared to a historical record of valence measures associated with the individual. For example, a series of consecutive negative valence measures may be indicative of an episode of depression.

After examining the valence measure(s), the health management platform can identify any variations indicative of health state (step 703), and then assess a health state of the individual (step 704). Valence measures may be more useful when compared to valence measures associated with prior journal entries produced by the individual. Said another way, valence measures associated with an individual may provide more personalized context when compared to other valence measures associated the individual rather than predetermined thresholds, patterns, etc.

These variation(s) can be stored in a memory accessible to the health management platform. The valence measure(s) and/or the health state assessment may also be stored in the memory for further review. Moreover, as noted above, an assessment of a certain health states may provoke the health management platform to perform a specific action. For example, if the health management platform determines that the individual is likely suffering from depression, then the health management platform may cause uplifting media content to be shown to the individual, transmit a notification to some other electronic device, etc.

To assess the health state of the individual, the health management platform may determine whether the individual should be classified in a depressed state or a non-depressed state, whether depression severity exceeds a specific level (e.g., as defined by clinical surveys), or whether a change in depression status/severity has occurred (e.g., as defined by clinically meaningful criteria). The health management platform may determine how to classify the individual based on information derived from self-reporting, passive sensor analytics, or any combination thereof.

Unless contrary to physical possibility, it is envisioned that the steps described above may be performed in various sequences and combinations. For example, the health management platform may periodically execute these processes such that health state is determined on a periodic basis (e.g., monthly, weekly, or daily). Such a feature enables the health management platform to continually monitor health state so that changes in the health state can be rapidly identified.

Other steps may also be included in some embodiments. For example, if the health management platform determines that the individual has been classified in a critical health state (e.g., a depressed state), the health management platform could surface a recommendation that prompts the individual to contact a healthcare provider, surface a notification (e.g., in the form of an email, text message, automated phone call, etc.) that prompts the individual to try an ecological momentary intervention by the health management platform (e.g., cognitive behavioral therapy intervention), or surface a notification that prompts a healthcare provider to contact the individual.

Processing System

Figure 8:
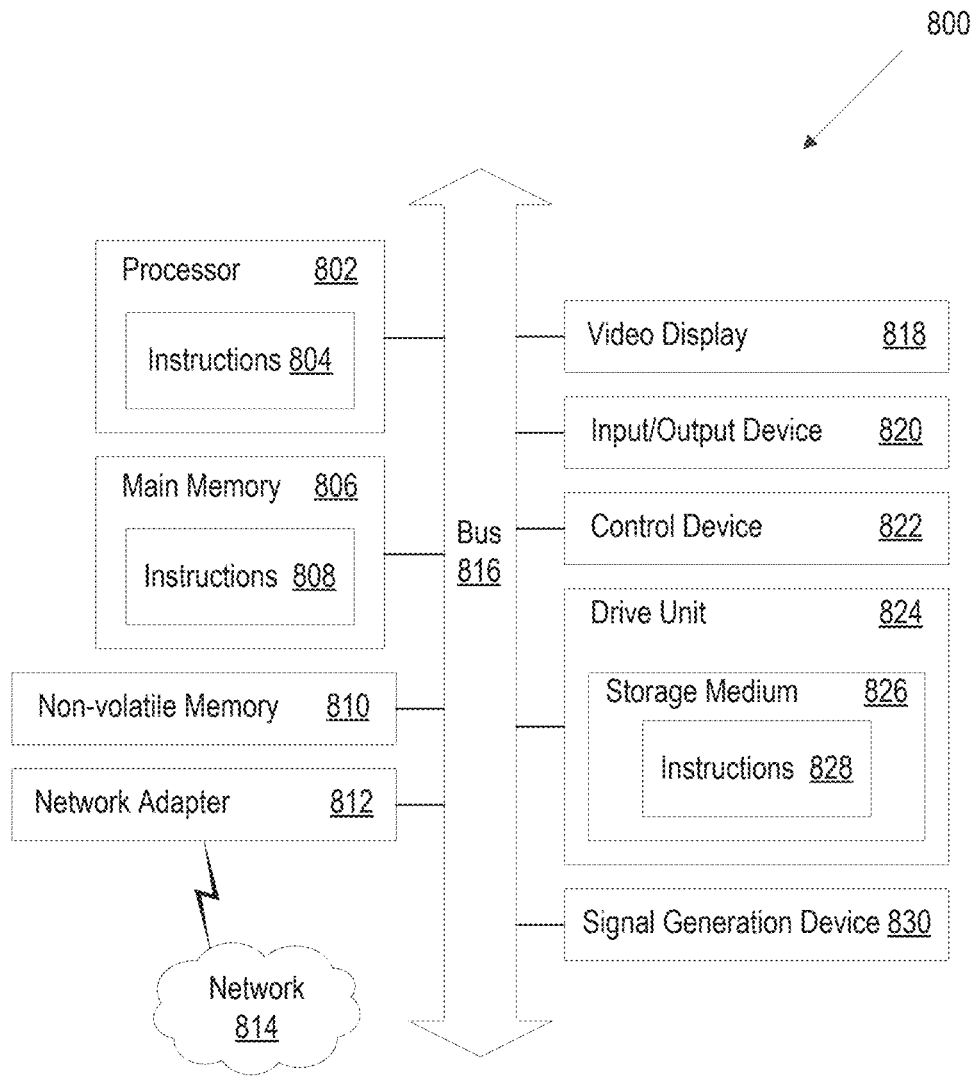
FIG. 8 is a block diagram illustrating an example of a processing system in which at least some operations described herein can be implemented.

FIG. 8 is a block diagram illustrating an example of a processing system 800 in which at least some operations described herein can be implemented. For example, some components of the processing system 800 may be hosted on an electronic device that includes a health management platform (e.g., health management platform 200 of FIG. 2).

The processing system 800 may include one or more central processing units ("processors") 802, main memory 806, non-volatile memory 810, network adapter 812 (e.g., network interface), video display 818, input/output devices 820, control device 822 (e.g., keyboard and pointing devices), drive unit 824 including a storage medium 826, and signal generation device 830 that are communicatively connected to a bus 816. The bus 816 is illustrated as an abstraction that represents one or more physical buses and/or point-to-point connections that are connected by appropriate bridges, adapters, or controllers. The bus 816, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 800 may share a similar computer processor architecture as that of a desktop computer, tablet computer, personal digital assistant (PDA), mobile phone, game console, music player, wearable electronic device (e.g., a watch or a fitness tracker), network-connected ("smart") device (e.g., a television or a home assistant device), virtual/augmented reality systems (e.g., a head-mounted display), or another electronic device capable of executing a set of instructions (sequential or otherwise) that specify action(s) to be taken by the processing system 800.

While the main memory 806, non-volatile memory 810, and storage medium 826 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 828. The term "machine-readable medium" and "storage medium" shall also be taken to include any medium that is capable of storing, encoding, or carrying a set of instructions for execution by the processing system 800.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 804, 808, 828) set at various times in various memory and storage devices in a computing device. When read and executed by the one or more processors 802, the instruction(s) cause the processing system 800 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 810, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 812 enables the processing system 800 to mediate data in a network 814 with an entity that is external to the processing system 800 through any communication protocol supported by the processing system 800 and the external entity. The network adapter 812 can include a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 812 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method for assessing health of an individual using a distributed system that includes (i) a computer server on which a health management platform is executing and (ii) an electronic device on which a computer program is executing, the method comprising:

monitoring, by the computer program, a location of the electronic device so as to establish when the electronic device is located proximate to a predetermined location;

generating, by the computer program, a notification that prompts the individual to create an audio recording in response to a determination that the electronic device is located proximate to the predetermined location;

applying, by the computer program, a noise reduction algorithm to improve signal-to-noise (SNR) ratio of audio media that is recorded by the electronic device and that is representative of the audio recording created by the individual, prior to transmitting the audio media to the health management platform;

transmitting, by the computer program, the audio media to the health management platform over a network via which the electronic device is communicatively connected to the computer server;

processing, by the health management platform, the audio media using an algorithm that objectively characterizes a frequency-domain feature and produces, as output, a value for the frequency-domain feature;

verifying, by the health management platform, an identity of the individual based on a comparison of the value produced for the frequency-domain feature to a reference value that is known to be representative of the individual; and in response to verifying the identity of the individual, establishing whether the individual has experienced a change in health based on the value produced for the frequency-domain feature.

2. The method of claim 1, wherein the frequency-domain feature is pitch, center formant frequency, shimmer, or jitter.

3. The method of claim 1, further comprising:

parsing, by the health management platform, the audio media to identify portions, if any, that include a voice of someone other than the individual; and removing, by the health management platform, the portions such that the algorithm is applied only to audio media that includes a voice of the individual.

4. The method of claim 1,
wherein the method further comprises:
- applying, by the health management platform, a second algorithm that objectively characterizes a second frequency-domain feature and produces, as output, a second value for the second frequency-domain feature; and wherein said determining and said establishing are further based on the second value produced for the second frequency-domain feature.

5. The method of claim 1,
wherein the method further comprises:
- applying, by the health management platform, a second algorithm that objectively characterizes a time-domain feature and produces, as output, a second value for the time-domain feature; and wherein said determining and said establishing are further based on the second value produced for the time-domain feature.

6. The method of claim 1, further comprising:
storing, by the health management platform, the value produced for the frequency-domain feature in a data structure that includes prior values produced for the frequency-domain feature over time and that is representative of a digital profile maintained for the individual.

7. The method of claim 6, wherein said establishing comprises determining that the value produced for the frequency-domain feature differs from at least one prior value produced for the frequency-domain feature by more than a predetermined amount, based on comparing the value produced for the frequency-domain feature to the prior values in the data structure.

8. The method of claim 1, further comprising:
in response to a determination that the individual has experienced a change in health,
- identifying, by the health management platform, interactive feedback that includes a recommendation for addressing the change in health; and
- transmitting, by the health management platform, the interactive feedback to the electronic device for display to the individual by the computer program.

9. The method of claim 1, further comprising:
in response to a determination that the individual has experienced a change in health,
- transmitting, by the health management platform, an indication of whether the predetermined location provoked positive valence or negative valence to the electronic device for display to the individual by the computer program.

\* \* \* \* \*